(12) United States Patent
Kumagai et al.

(10) Patent No.: US 7,060,821 B2
(45) Date of Patent: Jun. 13, 2006

(54) OSTEOCLAST DIFFERENTIATION INHIBITORS

(75) Inventors: Hiroyuki Kumagai, Kanagawa (JP); Tomohiro Sameshima, Kanagawa (JP); Motoko Matsufuji, Tokyo (JP); Naoto Kawamura, Kanagawa (JP); Kunio Isshiki, Kanagawa (JP); Hiroyuki Inoue, Shizuoka (JP); Tetsuya Someno, Saitama (JP); Masaaki Ishizuka, Tokyo (JP); Tomio Takeuchi, Tokyo (JP)

(73) Assignees: Mercian Corporation, Tokyo (JP); Zaidan Hojin Biseibutsu Kagaku Kenkyu Kai, Tokyo (JP)

( * ) Notice: Subject to any disclaimer, the term of this patent is extended or adjusted under 35 U.S.C. 154(b) by 82 days.

(21) Appl. No.: 10/506,975

(22) PCT Filed: Mar. 6, 2003

(86) PCT No.: PCT/JP03/02633

§ 371 (c)(1), (2), (4) Date: Sep. 16, 2004

(87) PCT Pub. No.: WO03/076639

PCT Pub. Date: Sep. 18, 2003

(65) Prior Publication Data

US 2005/0124050 A1    Jun. 9, 2005

(30) Foreign Application Priority Data

Mar. 8, 2002 (JP) ............................. 2002-063046

(51) Int. Cl.
*C07D 498/02* (2006.01)
*C07D 295/02* (2006.01)

(52) U.S. Cl. .................. 544/101; 544/102; 435/118

(58) Field of Classification Search ............... 544/101, 544/102
See application file for complete search history.

(56) References Cited

OTHER PUBLICATIONS

Inoue et al. J. Antibiot (Tokyo) Mar. 2003; 56(3):209-13.*
Someno et al. J. Antibiot (Tokyo) Mar. 2003; 56(3):214-218.*
Levine S.G. et al—Structure of the o-Aminophenol-Adipoin Condensation Product—J. Org. Chem. 1976, vol. 41, No. 25, p. 4026-4028.
Herzig C. et al—2-Chlorooxirane als Synthone zur Darstellung sechsgliedriger Heterocyclen—Chem. Ber. 1981, vol. 114, N. 6, p. 2348-2354.

* cited by examiner

*Primary Examiner*—Kahsay Habte
(74) *Attorney, Agent, or Firm*—Stevens, Davis, Miller & Mosher, L.L.P.

(57) ABSTRACT

A compound represented by formula (I); a process for producing a compound (substance F-1490) of formula (I), wherein X represents —O— and R represents a hydroxyl group, by using a microorganism belonging to the genus *Cunninghamella*; and a *Cunninghamella* sp. F-1490 strain (FERM BP-8287) capable of producing the substance F-1490; and an osteoclast differentiation inhibitory agent containing as an active ingredient the compound represented by formula (I):

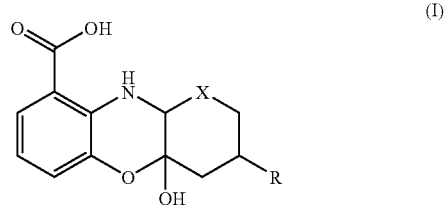

(I)

wherein X represents —O— or —CH$_2$—, and R represents a hydroxyl group when X represents —O—, or a hydrogen atom when X represents —CH$_2$—.

3 Claims, 6 Drawing Sheets

OSTEOCLAST DIFFERENTIATION INHIBITORS

TECHNICAL FIELD

The present invention relates to a compound represented by formula (I):

wherein the symbols have the same meanings as described hereinbelow, a process for producing a compound (substance F-1490) of formula (I), wherein X represents —O— and R represents a hydroxyl group, by using a microorganism belonging to the genus *Cunninghamella*; a *Cunninghamella* sp. F-1490 strain (FERM BP-8287) capable of producing the substance F-1490; and an osteoclast differentiation inhibitory agent comprising the compound represented by formula (I) as an active ingredient.

BACKGROUND ART

Osteoclasts are cells generated by differentiation of bone marrow cells and known to be involved in a number of diseases such as osteometastasis of cancer cells including breast cancer cells, rheumatoid arthritis, and osteoporosis. Accordingly, it is presumed that successful suppression of the differentiation from bone marrow cells into osteoclasts will result in excellent therapeutic effects on the aforementioned diseases. Thus, it has been desired to develop substances that have low toxicities and exhibit potent inhibitory effects against the differentiation from bone marrow cells into osteoclasts. However, no reports have been issued until now on substances having such properties as mentioned above among low molecular weight substances derived from microorganisms.

DISCLOSURE OF THE INVENTION

It is an object of the present invention to provide a novel compound that has low toxicities and exhibits an osteoclast differentiation inhibiting effect; a process for producing the compound; a novel microorganism having the capability of producing such a compound; and an osteoclast differentiation inhibiting agent containing as an active ingredient the compound.

Note that the term "osteoclast differentiation inhibition" as used herein means inhibiting the differentiation from bone marrow cells into osteoclasts.

To attain the above-mentioned object, the present inventors isolated microorganisms from soils of various geographical areas and extensively studied metabolites produced by the microorganisms. As a result, they have found that a microorganism belonging to the genus *Cunninghamella* newly isolated produced in the culture broth a substance that shows osteoclast differentiation inhibiting activity. Separation and purification of the active substance from the culture broth and investigation of the physicochemical properties allowed the inventors to confirm that the obtained active substance is a novel compound represented by formula (I) described below that differs from any known substance and has excellent osteoclast differentiation inhibiting activity.

Further, the present inventors have synthesized novel analogue compounds or formula (II) that have a structure similar to that of the compound represented by formula (I) and examined the properties thereof. The results obtained allowed the inventors to confirm that the analogue compounds had likewise osteoclast differentiation inhibiting activity at low concentrations. The present invention has been achieved based on these findings.

That is, the present invention relates to a novel compound having osteoclast differentiation inhibiting activity described below or salts thereof; a process for producing the compound; a microorganism that produces the compound; and a drug that contains as an active ingredient the compound.

1. A compound represented by formula (I):

wherein X represents —O— or —$CH_2$—, and R represents a hydroxyl group when X represents —O—, or a hydrogen atom when X represents —$CH_2$—, or salts thereof.

2. The compound according to 1 above, wherein in formula (I), X represents —O— and R represents a hydroxyl group, or salts thereof.

3. The compound according to 1 above, wherein in formula (I), X represents —$CH_2$— and R represents a hydrogen atom, or salts thereof.

4. A process for producing the compound according to 2 above, including cultivating a microorganism that belongs to the genus *Cunninghamella* and is capable of producing the compound according to 2 above, and recovering the compound according to 2 above from the resultant culture broth.

5. *Cunninghamella* sp. F-1490 strain (FERM BP-8287) having a capability of producing the compound according to 2 above.

6. An osteoclast differentiation inhibitory agent containing as an active ingredient the compound or salts thereof according to 1 above.

Hereinafter, the present invention will be described in detail.

The present inventors named a compound among the compounds represented by formula (I), in which X represents —O— and R represents a hydroxyl group, a substance F-1490.

The substance F-1490 is a novel substance that is clearly distinguished from known compounds by the molecular formula, physicochemical properties and structural characteristics.

Salts of the substance F-1490 of the present invention include salts with pharmaceutically acceptable bases (inorganic bases and organic bases), for example, salts with inorganic bases such as sodium salt, potassium salt, ammonium salt, calcium salt, magnesium salt and aluminum salt, salts with basic amino acids (for example, arginine, lysine, etc.) and so on.

Further, the present invention provides a process for producing the substance F-1490 by cultivating a microorganism belonging to the genus *Cunninghamella* and having the capability of producing the substance F-1490 that exhibits osteoclast differentiation inhibiting activity and recovering the substance F-1490 from the resulting culture broth; a microorganism belonging to the genus *Cunninghamella* that has the capability of producing the substance F-1490; and osteoclast differentiation inhibitory agents that contain as an active ingredient the substance F-1490.

The microorganism used in the present invention may be any microorganism as long as it is a strain that belongs to the genus *Cunninghamella* and has the capability of producing the substance F-1490 of the present invention. Search for such a microorganism can be performed, for example, as follows. That is, extracts of various microorganism culture broths are added to culture broth of bone marrow cells and the number of tartaric acid resistant acid phosphatase-positive cells, which is an index of differentiation into osteoclasts, is measured. The target microorganism that has the capability of producing the substance F-1490 can be obtained by isolating and identifying an active substance from culture broth of the microbe that shows a decrease in the number of cells, that is, shows inhibition of the differentiation into osteoclasts.

Examples of the microorganism found in this manner include a strain F-1490 that was isolated from soil by the present inventors and belongs to the genus *Cunninghamella*. However, the microorganism is not limited to this strain but all the strains can be used in the present invention so far as they belong to the genus *Cunninghamella* and have the capability of producing the substance F-1490 of the present invention, including mutants thereof, for example, artificial mutants obtained by treatments with mutagens such as ultraviolet rays, X rays, radiations and chemicals as well as spontaneous mutants.

Hereinafter, mycological properties of the strain F-1490 will be explained.

Inoculation of this strain on potato dextrose agar (hereinafter, referred to as "PDA"), malt extract agar (hereinafter, referred to as "MEA"), oatmeal agar (hereinafter, referred to as "OA") and cultivation at 25° C. resulted in wool-like hyphae, the color of which was initially white (A1) and subsequently turned cream (4A3) via yellowish white (4A2) on all the agar plates.

The growth rate is extremely high; the hyphae covered all over the surface of a dish of 85 mm in diameter in all the plates under the condition of cultivation for three days. The growth is very vigorous such that after one week, the lid of the dish is lifted. Further, in all the plates, no production of soluble pigments is observed. Note that the descriptions on color tone are made according to Methuen Handbook of Colour (Kornerup & Wanscher, 1978).

The morphological characteristics of the strain are as follows. Under an optical microscope, only peculiar sporangiophores are observed but not sporocarps. Aerial hyphae have few septa and also have stolons. Formation of rhizoids is also confirmed. Sporangiophores are formed monogenically from aerial hyphae such as stolons. The stipes are smooth and grow linearly. The stipes have vesicles at their apices below which irregular or whorled branchings are observed. The branchings have small vesicles on their apices. The vesicles are spheroidal to oval with a width of 30 µm at the apices or a maximum of 20 µm in the branchings.

The strain has neither sporangium nor merosporangium but has unilocular sporangiolum that arises on the surface of the vesicles. The sporangiolum is globose to ellipsoidal and is of a size of 6 to 9 µm. The sporangiolum is brown and its surface is short-echinulate. No stria are observed.

From the mycological properties mentioned above, the present inventors judged that the strain belongs to the genus *Cunninghamella*, named it *Cunninghamella* sp. F-1490 and deposited it on Oct. 2, 2001 at the independent administrative corporation, National Institute of Advanced Industrial Science and Technology, International Patent Organism Depositary at Chuo Dai-6, 1-1 Higashi 1-Chome, Tsukuba-shi, Ibaraki-ken, Japan, as the accession number of FERM P-18548, and transferred from the original deposit to international deposit based on Budapest Treaty on Jan. 31, 2003, and deposited as the accession number of FERM BP-8287.

The substance F-1490 of the present invention can be produced by inoculating the above-mentioned strain in a nutrient source-containing medium and cultivating it aerobically. The substance F-1490 producing microorganism is not limited to the above-mentioned strain but all the strains that belong to the genus *Cunninghamella* and have the capability of producing the substance F-1490 may be used in the present invention.

The method of cultivating the above-mentioned microorganisms is in principle pursuant to the cultivation method for general microorganisms. Usually, it is preferable that the method is practiced under aerobic conditions, such as shaking culture by liquid culture or aeration agitation culture. The medium that is used for cultivation maybe any medium that contains nutrient source available to the microorganisms belonging to the genus *Cunninghamella*. Various synthetic and semi-synthetic media as well as natural media are available. The composition of medium is as follows. Carbon sources including glucose, sucrose, fructose, glycerol, dextrin, starch, molasses and so on may be used singly or in combination. Nitrogen sources including organic nitrogen sources such as pharmamedia, peptone, meat extract, soybean powder, casein, amino acids, yeast extract and urea may be used singly or in combination. In addition, salts such as sodium chloride, potassium chloride, calcium carbonate, magnesium sulfate, sodium phosphate, potassium phosphate and cobalt chloride, heavy metal salts, vitamins such as vitamin B and biotin may be added as necessary.

In case considerable foaming occurs during the cultivation, various defoaming agents may be added in the medium as appropriate. When the defoaming agent is added, care must be taken to add the defoaming agent in a concentration that does not adversely affect production of the target substance. It is desirable that the pH of the medium is about 5 to about 9, usually around neutrality. The cultivation temperature is recommended to be kept at usually 10 to 40° C., preferably 20 to 27° C. The cultivation time is about 2 to about 14 days, usually 3 to 5 days. Needless to say, various cultivation conditions described above may be varied depending on the kind and characteristics of the microorganism used, external conditions and so on as appropriate and optimal conditions can be selected. The substance F-1490 of the present invention which accumulates in the culture broth can be recovered by separating the fungus body by using known ordinary solid-liquid separation means such as filtration and centrifugation; and extracting the target compound from the filtrate.

Separation and purification of the substance F-1490 can be performed by selecting and combining various known methods. For example, a solvent extraction method using ethyl acetate, n-butanol or the like, and a column chromatographic method using a carrier, for example, polystyrene-based adsorbent resin such as Amberlite XAD (manufactured by Rohm and Haas Co., Ltd.) and Diaion HP-20 (manufactured by Mitsubishi Chemical Corporation), silica gel, alumina or activated carbon may be used. The method of eluting the target substance from the carriers may vary depending on the kind and properties of the carrier. For example, in the case of polystyrene-based adsorbent resin, hydroalcohol, hydroacetone and the like can be used as eluting solvents. Further, gel filtration using Sephadex LH-20 (manufactured by Pharmacia AB), Bio Gel P-2 (manufactured by Bio-Rad Laboratories) or the like, thin layer chromatography using silica gel, alumina or the like, preparative high performance liquid chromatography (preparative HPLC) using a normal phase or reversed phase column and so on may be used. These methods may be used singly or in combination as appropriate, or in repetitions as appropriate to effect separation and purification.

The substance F-1490 thus obtained has the following physicochemical properties.

(1) Form: white powder, (2) Molecular formula: $C_{12}H_{13}NO_6$
(Measurement of $C_{12}H_{14}NO_6$ by high resolution FAB mass spectrometry Calculated m/z: 268.0821 $(M+H)^+$, Found m/z: 268.0861), (3) Specific optical rotation: $[\alpha]_D^{22}$ −57.5° (c 0.4, methanol)

(4) Melting point: 125 to 131° C. (dec.)

Figure 1:
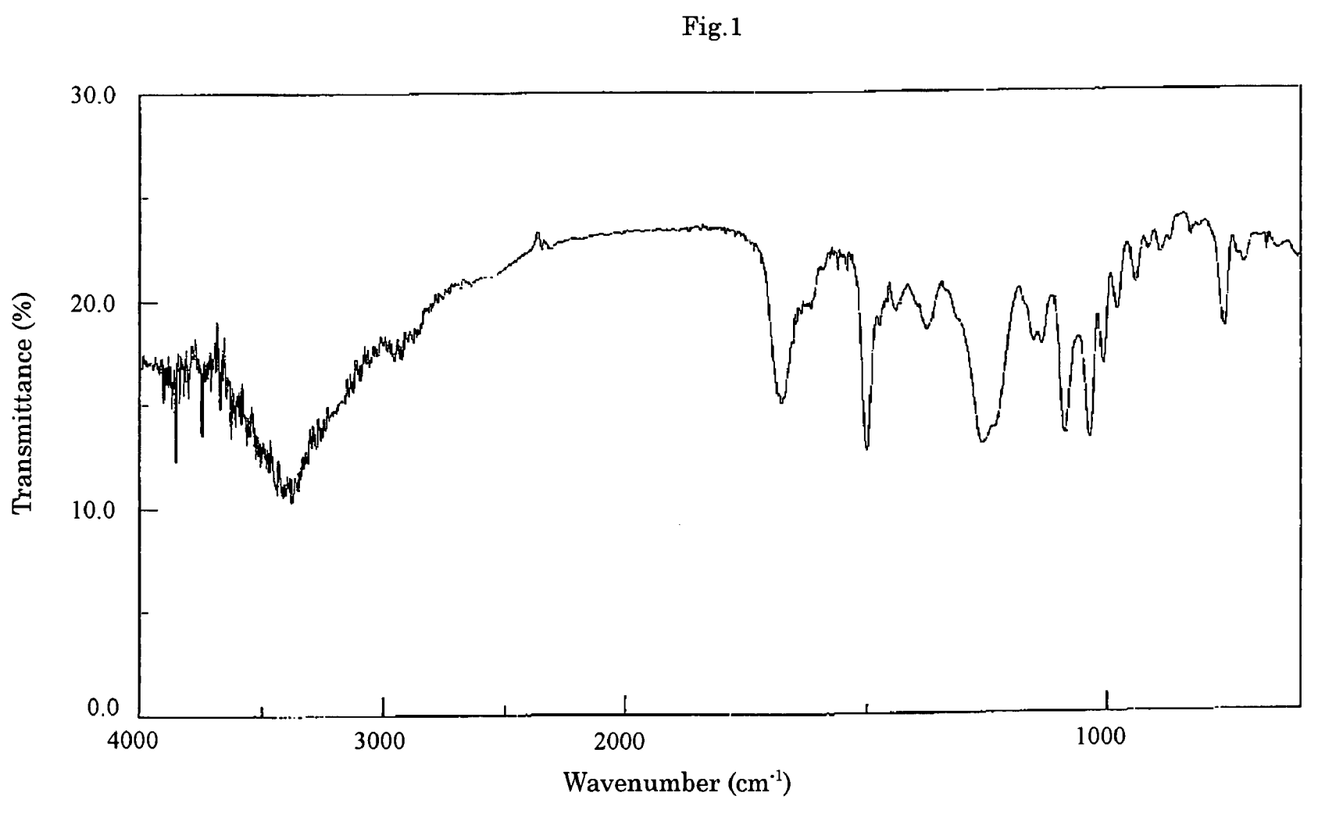
FIG. 1 is a diagram showing an infrared absorption spectrum of the substance F-1490 by the KBr method.

(5) Infrared absorption spectrum: The results obtained by measurements by the KBr method are as shown in FIG. 1. The characteristic absorptions are as follows.

$IR\nu_{max}$ (KBr) $cm^{-1}$: 3380, 1680, 1620, 1500, 1440, 1375, 1260, 1090, 1035.

Figure 2:
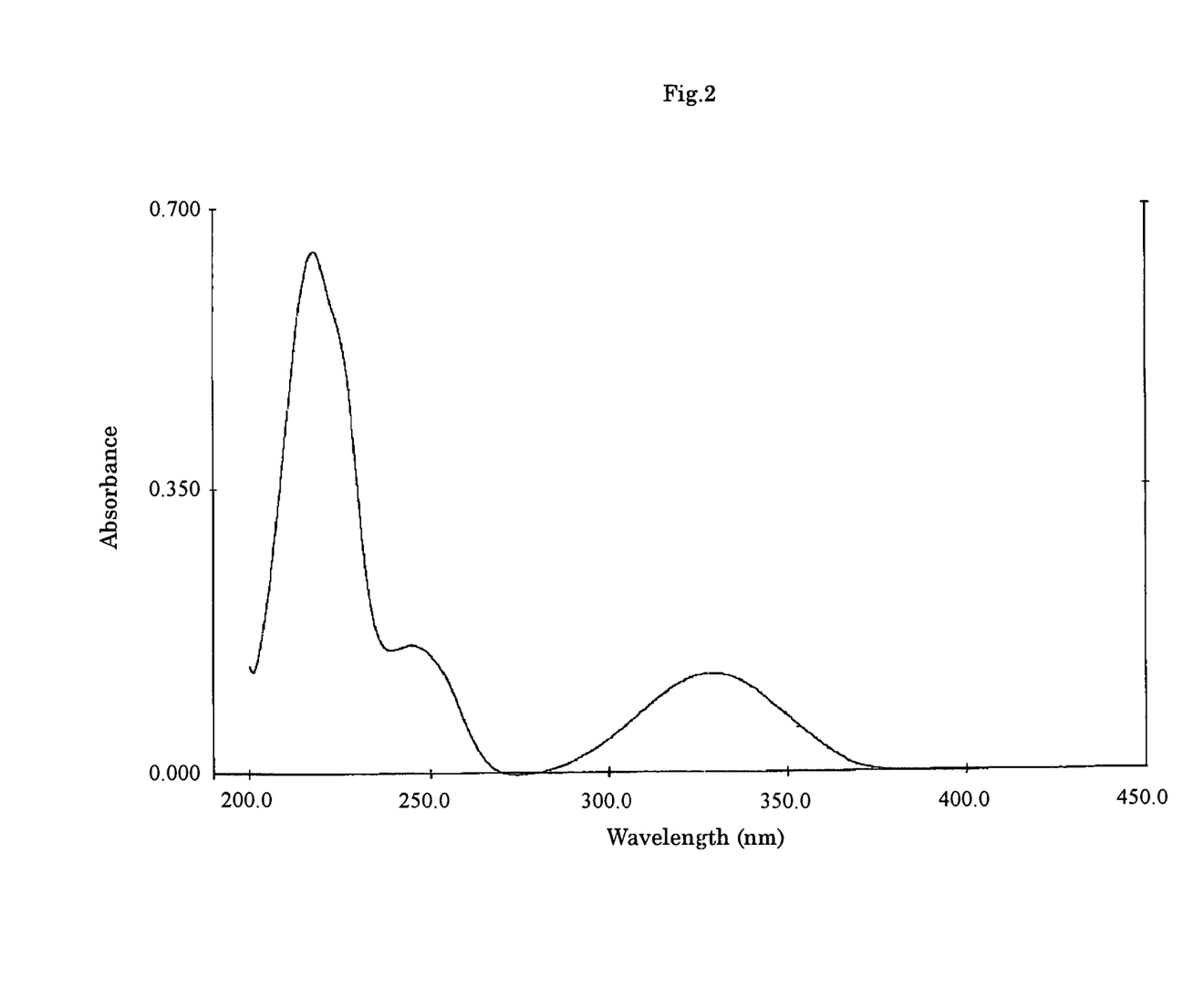
FIG. 2 is a diagram showing an ultraviolet absorption spectrum of the substance F-1490 measured in a methanol solution.

(6) Ultraviolet absorption spectrum: The results obtained by measurements in methanol are as shown in FIG. 2. The characteristic absorptions are as follows.

$UV\lambda_{max}$ nm: 217, 245 (sh), 328.

(7) Solubility: Readily soluble in ethyl acetate, methanol, dimethyl sulfoxide and water; hardly soluble in hexane.

Figure 3:
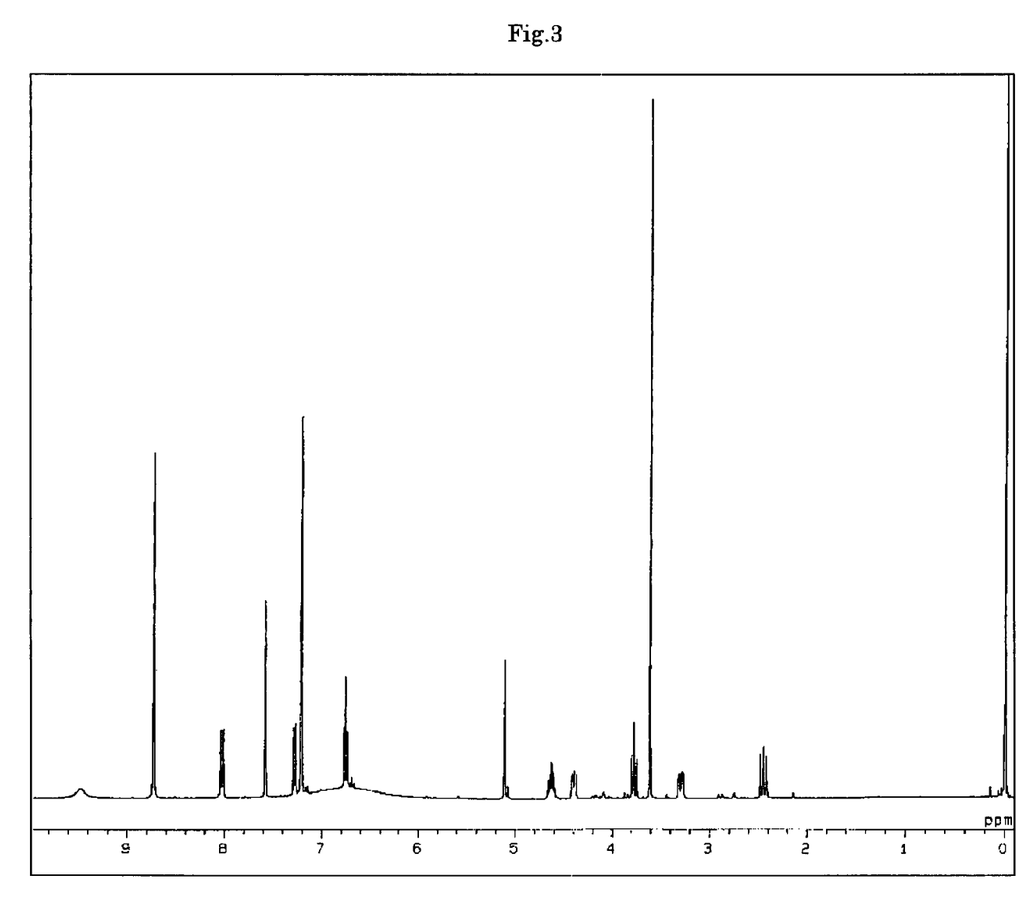
FIG. 3 is a diagram showing $^1$H-nuclear magnetic resonance spectrum of the substance F-1490 measured in a heavy pyridine solution.

(8) $^1H$-nuclear magnetic resonance spectrum: The results obtained by performing measurement by dissolving the substance in heavy pyridine and using tetramethylsilane as internal standard are as shown in FIG. 3. Chemical shift, multiplicity and spin coupling constant of each signal are as follows.

δ 8.01 (1H, dd, J=1.8 Hz), δ 7.28 (1H, dd, J=1.8 Hz), 6.76 (1H, t, J=8 Hz), 5.12 (1H, s), 4.64 (1H, m), 4.40 (1H, ddd, J=2, 5.11 Hz), 3.78 (1H, dd, J=11.11 Hz), 3.30 (1H, ddd, J=2, 5.13 Hz), 2.45 (1H, dd, J=11.13 Hz).

Figure 4:
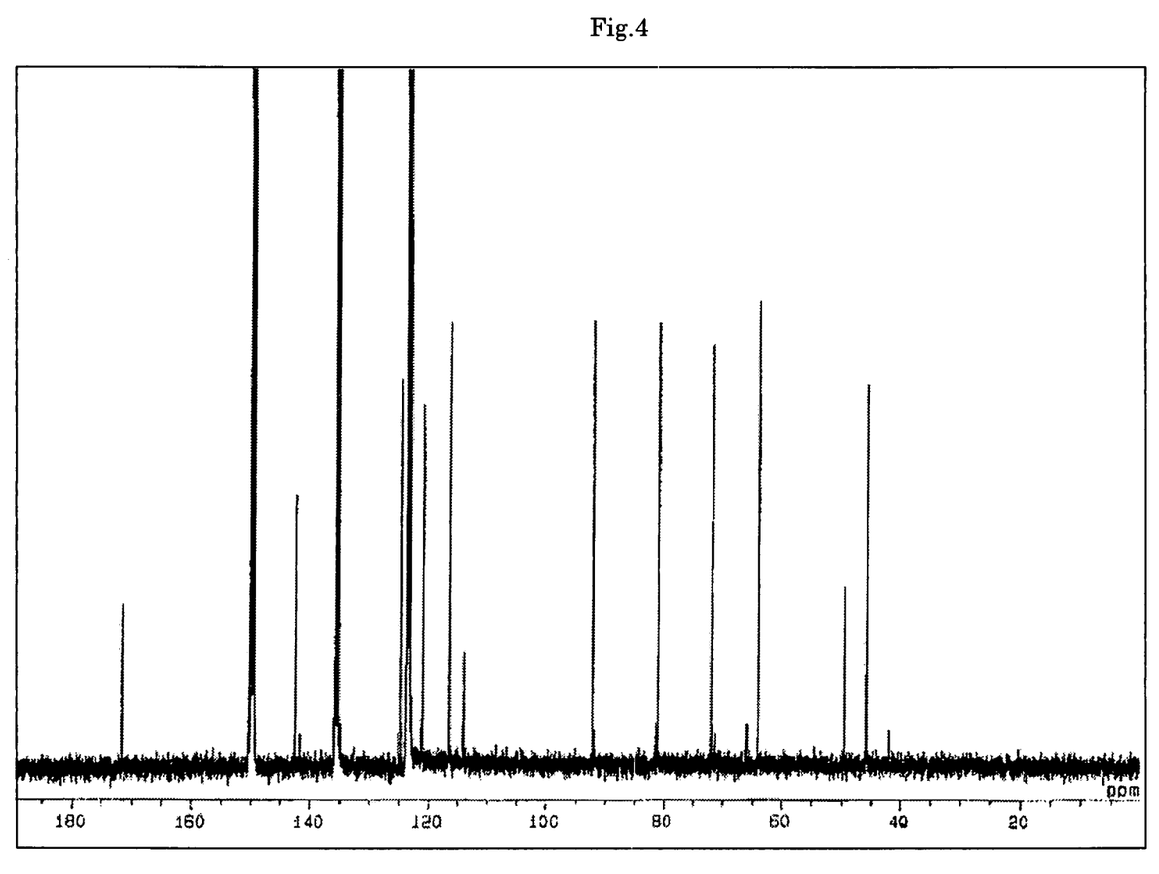
FIG. 4 is a diagram showing $^{13}$C-nuclear magnetic resonance spectrum of the substance F-1490 measured in a heavy pyridine solution.
Figure 5:
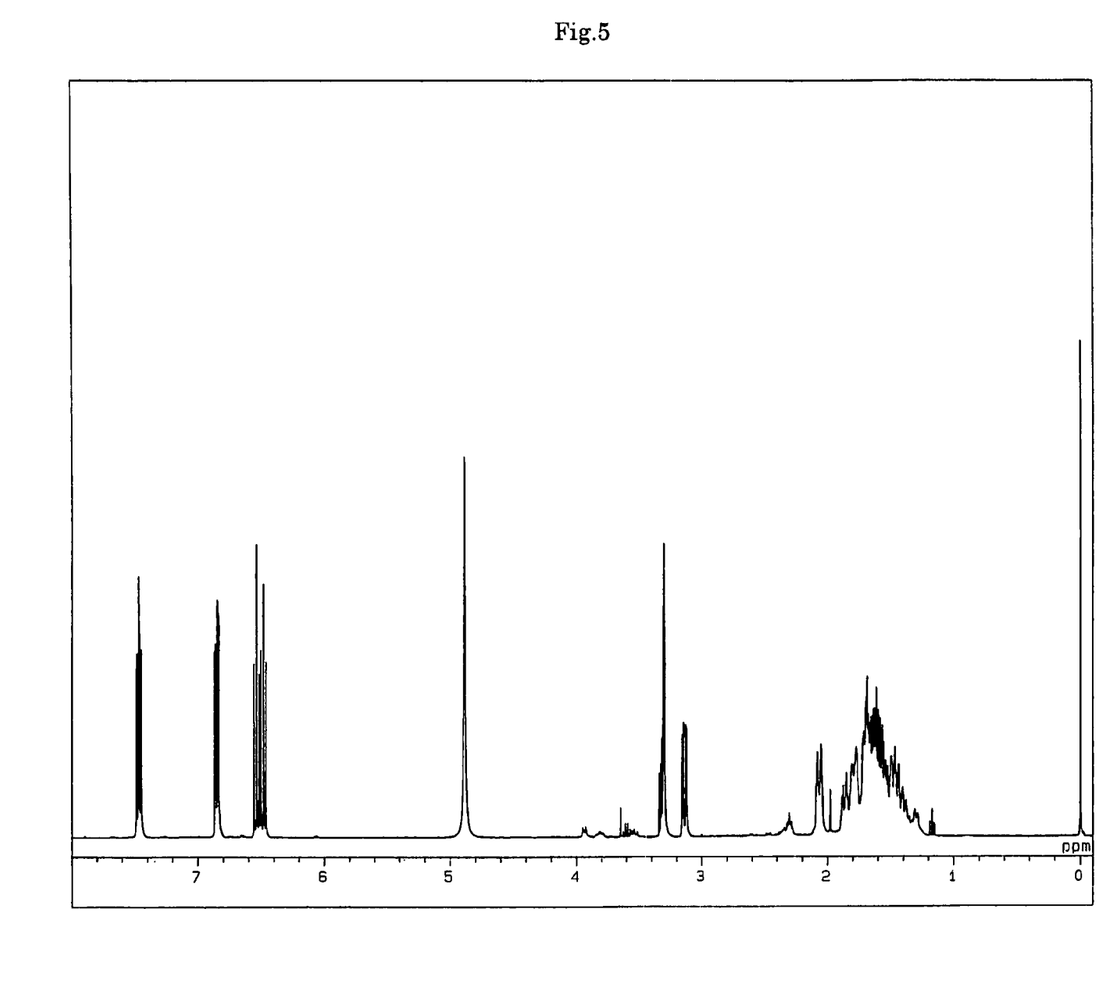
FIG. 5 is a diagram showing $^1$H-nuclear magnetic resonance spectrum of the substance F-1490-A measured in a heavy methanol solution.
Figure 6:
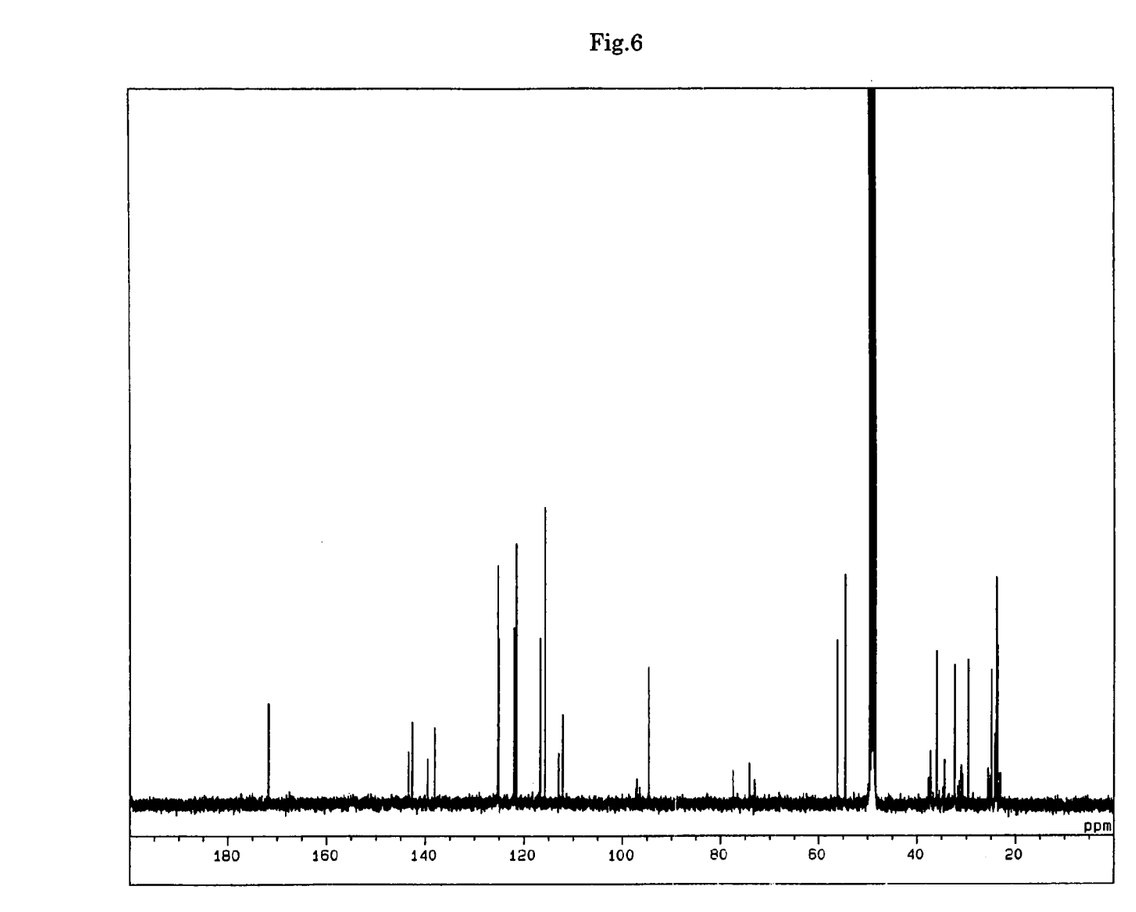
FIG. 6 is a diagram showing $^{13}$C-nuclear magnetic resonance spectrum of the substance F-1490-A measured in a heavy methanol solution.

(9) $^{13}C$-nuclear magnetic resonance spectrum: The results obtained by measurements as dissolved in heavy pyridine and using tetramethylsilane as internal standard are as shown in FIG. 4. Chemical shift and multiplicity of each signal are as follows.

δ 171.7(s), 142.6(s), 135.6(s), 124.8(d), 121.1(d), 116.6 (d), 114.1(s), 92.3(s), 81.2(d), 72.0(t), 64.1(d), 45.9(t).

Further, the present inventors synthesized a novel analogue having a chemical structure similar to that of the substance F-1490, represented by formula (I) in which X represents —$CH_2$— and R represents a hydrogen atom (hereinafter, referred to as "F-1490-A") (see Example 2 described later) and tested it together with the substance F-1490 for their physiological activity.

The substances F-1490 and F-1490-A of the present invention have excellent osteoclast differentiation inhibiting activity and in addition low toxicity to cells, so that it is expected that they can be used as therapeutic agents for diseases that accompany an increase in the activity of osteoclasts, for example, osteometastasis of cancer cells, rheumatoid arthritis, osteoporosis and so on.

The osteoclast differentiation inhibiting activity of the substances of the present invention can be measured, for example, by the method described below.

Bone marrow cells were collected from a C57BL/6mouse (female, 6 weeks old) and suspended in RPMI1460 medium that contains 10% fetal calf serum, 1 mM pyruvic acid, 0.1 mM non-essential amino acids (manufactured by Gibco), 500 μM 2-mercaptoethanol, 200 ng/ml parathyroid hormone related protein (PTHrP) and 50 μg/ml L-ascorbic acid and 1 ml of the suspension adjusted to a cell population of $1.5 \times 10^6$ cells/well was inoculated on a 24-well microplate. At the same time a test sample was added in appropriate amounts. On days 2 and 4 from the start of the cultivation, half the amount of the medium is exchanged with fresh medium containing the test sample. On day 7 from the start of the cultivation, the medium is removed by suction and the cells are fixed with an acetone:methanol (1:1) solution, to thereby allow tartaric acid-resistant acid phosphatase-positive cells stained. That is, 0.4 ml of a 0.2-M acetate buffer (pH 5.2) containing a staining fluid (0.1 mg/ml Naphthol AS-MX phosphate (Sigma AB), 0.6 mg/ml Fast red violet LB sal (Sigma AB) and 20 mM tartaric acid is added to each well and the resultants are allowed to react at 37° C. for 1 hour. After color development, the number of tartaric acid-resistant acid phosphatase-positive cells, which is an index of differentiation into osteoclasts, is measured under a microscope.

When the test sample contains a substance that is effective for inhibition of osteoclast differentiation, the occurrence of tartaric acid-resistant acid phosphatase-positive cells is inhibited. From changes in the above-mentioned number of cells depending on the concentration of the test sample, an effective concentration range of the test sample can be obtained.

The substances F-1490 and F-1490-A of the present invention inhibited the differentiation of bone marrow cells into osteoclasts in low concentrations as shown in Table 1 below.

TABLE 1

| Concentration | Inhibition rate of differentiation into osteoclasts (%) | |
|---|---|---|
| (μg/ml) | Substance F-1490 | Substance F-1490-A |
| 0 | 0 | 0 |
| 0.20 | 6 | 2 |
| 0.78 | 50 | 63 |
| 3.10 | 69 | 74 |
| 12.50 | 98 | 87 |
| 50% growth inhibition concentration (μg/ml) | 0.78 | 0.65 |

Further, the substances F-1490 and F-1490-A of the present invention showed substantially no toxicity to various kinds of cultivated cells as shown in Table 2 below.

TABLE 2

| | 50% growth inhibition concentration (μg/ml) | |
|---|---|---|
| Cells | Substance F-1490 | Substance F-1490-A |
| L1210 | >50 | >50 |
| Colon26 | >50 | >50 |
| B16BL6 | >50 | >50 |

Note that the tests were performed as follows. Various kinds of murine cancer cells (L1210 (leukemia)), Colon 26 (colon cancer), B16BL6 (malignant melanoma)) were suspended in RPMI1640 medium containing 10% fetal calf serum and adjusted to $2 \times 10^4$ cells/well and 0.1 ml of each of the suspensions was seeded on a 96-well plate. At the same time, a predetermined amount of the substance F-1490 was added and the resultants were cultivated at 37° C. for 48 hours in the air containing 5% $CO_2$. Further, 10 µl of 0.5% MTT (3-[4,5-dimethylthiazol-2-yl] 2,5-biphenyl tetrazolium bromide) was added and the resultants were cultivated for 4 hours. After the cultivation, 0.1 ml of 10% SDS-0.01N hydrochloric acid was added and absorbance at 570 nm was measured to determine 50% growth inhibition concentration.

BEST MODE FOR CARRYING OUT THE INVENTION

Hereinafter, the present invention will be described by examples. However, the present invention should not be considered to be limited by the following description.

EXAMPLE 1

Cultivation of the Substance F-1490-Producing Microorganism and Separation and Purification of the Substance F-1490

A loopful of a slant medium (potato dextrose agar) of *Cunninghamella* sp. F-1490 (FERM BP-8287) strain was inoculated in a 500-ml Erlenmeyer flask containing 50 ml of a starter medium (2% potato starch, 1% glucose, 2% soybean powder ("Esusan Meat", manufactured by Ajinomoto), 0.1% potassium dihydrogen phosphate and 0.05% magnesium sulfate, without pH adjustment) and incubated on a rotary shaker at 25° C. for 2 days to obtain a seed culture broth. A medium consisting of 4% glutinous starch syrup, 2% peptone (manufactured by Kyokuto Pharmaceutical Industrial Co., Ltd.), 1% yeastextract, 0.5% magnesium sulfate and 0.9% potassium dihydrogen phosphate was used as a production medium. 60 ml each of the medium was charged in a 500-ml Erlenmeyer flask and sterilized. Then 1% each of the seed culture was inoculated thereto. The flasks were incubated on a rotary shaker at 25° C. for 4 days and 20 liters of the obtained culture broth was centrifuged to separate it into a culture filtrate and fungus body.

After adjusted to pH 2 with 6N hydrochloric acid, the obtained culture filtrate was passed through a 5-liter column packed with adsorbent resin, Diaion HP-20 (manufactured by Mitsubishi Chemical Corporation) equilibrated with water. The HP-20 column on which the active ingredient adsorbed was washed with 10 liters of 20% aqueous methanol solution and then the active ingredient was eluted with 10 liters of methanol. The methanol was evaporated from the eluted solutions by using an evaporator and 2 liters of ethyl acetate was added to the residue and the resultant was stirred. The ethyl acetate layer was taken up and 2 liters of water was added thereto. While stirring, the mixture was adjusted to pH 8 with 1N aqueous sodium hydroxide solution. After leaving the mixture at rest to allow it to be separated into two layers, the water layer was separated and adjusted to pH 2 with 1N hydrochloric acid. Further, after 2 liters of ethyl acetate was added to effect extraction, the ethyl acetate layer was concentrated under reduced pressure to obtain 6.1 g of a brown oily substance.

The brown oily substance was dissolved in a small amount of methanol and the solution was coated on silica gel. The resultant was packed in a 400-ml silica gel column filled with chloroform. After it was washed with 1 liter of a chloroform-methanol mixed solution (15:1), the column was eluted with 1 liter of a chloroform-methanol mixed solution (10:1). The thus obtained active fraction was concentrated under reduced pressure to obtain 0.39 g of a yellow oily substance. Further, this was dissolved in a small amount of methanol and the solution was coated on silica gel and charged in a silica gel column (50 ml) filled with toluene. After it was washed with 150 ml of a toluene-acetone mixed solution (3:1), the column was eluted with 150 ml of a toluene-acetone mixed solution (2:1). Fractions containing the active substance were collected and concentrated under reduced pressure to obtain 106 mg of a yellow powdery substance.

The thus obtained yellow powdery substance was dissolved in a small amount of methanol and charged in a 200-ml Sephadex LH-20 column (manufactured by Pharmacia AB) and eluted with methanol. The active fractions were collected and concentrated under reduced pressure to obtain 20 mg of the substance F-1490.

EXAMPLE 2

Synthesis of the Substance F-1490-A

To a suspension of 100 mg of 3-hydroxyanthranilic acid and 400 mg of 1,2-cyclohexanedione in 20 ml of methanol was added 1 g of sodium borohydride in a small amount at a time over 30 minutes under ice-cooling with stirring. After completion of the addition, the mixture was stirred at room temperature for 1 hour and then ice-cooled again. The resultant was adjusted to pH 7 by addition of 1N hydrochloric acid and the solvent was evaporated under reduced pressure. The obtained residue was purified by preparative TLC (hexane-ethyl acetate 1:1) to obtain a single band that develops color at an Rf value of 0.6 with phosphorus molybdenum sulfate under heating to obtain 90 mg of the target substance F-1490-A.

$^1$H-NMR and $^{13}$C-NMR spectra indicated that the substance F-1490-A has a chemical structure shown below.

(II)

INDSUTRIAL APPLICABILITY

Since the substances F-1490 and F-1490-A have excellent osteoclast differentiation inhibiting activity and low toxicity to cultivated cells, it is anticipated that they can be utilized as therapeutic agents for diseases that accompany an increase in the activity of osteoclasts.

The invention claimed is:

1. A compound represented by formula (I):

(I)

wherein X represents —O— or —CH$_2$—, and R represents a hydroxyl group when X represents —O—, or a hydrogen atom when X represents —CH$_2$—, or salts thereof.

2. The compound according to claim 1, wherein in formula (I), X represents —O— and R represents a hydroxyl group, or salts thereof.

3. The compound according to claim 1, wherein in formula (I), X represents —CH$_2$— and R represents a hydrogen atom, or salts thereof.

* * * * *